(12) United States Patent
Maier et al.

(10) Patent No.: US 8,317,844 B2
(45) Date of Patent: Nov. 27, 2012

(54) DEVICE FOR FIXING A REFERENCE ELEMENT

(75) Inventors: Christian Maier, Munich (DE); Georg Maier, Munich (DE)

(73) Assignee: Brainlab AG, Feldkirchen (DE)

( * ) Notice: Subject to any disclaimer, the term of this patent is extended or adjusted under 35 U.S.C. 154(b) by 1360 days.

(21) Appl. No.: 11/553,606

(22) Filed: Oct. 27, 2006

(65) Prior Publication Data

US 2007/0122233 A1 May 31, 2007

Related U.S. Application Data

(60) Provisional application No. 60/754,553, filed on Dec. 28, 2005, provisional application No. 60/754,510, filed on Dec. 28, 2005.

(30) Foreign Application Priority Data

Oct. 27, 2005 (EP) ..................................... 05023516

(51) Int. Cl.
*F16B 9/00* (2006.01)
(52) U.S. Cl. ........................................ 606/300; 403/200
(58) Field of Classification Search .................... 606/60, 606/246–279, 300–331; 600/426–429
See application file for complete search history.

(56) References Cited

U.S. PATENT DOCUMENTS

| 4,759,350 | A | | 7/1988 | Dunn et al. | |
|---|---|---|---|---|---|
| 4,927,421 | A | | 5/1990 | Goble et al. | |
| 4,955,891 | A | * | 9/1990 | Carol | 606/130 |
| 5,133,342 | A | * | 7/1992 | Seaton | 602/39 |
| 5,312,412 | A | * | 5/1994 | Whipple | 606/96 |
| 5,613,971 | A | * | 3/1997 | Lower et al. | 606/96 |
| 5,688,285 | A | | 11/1997 | Yamada | |
| 5,910,141 | A | * | 6/1999 | Morrison et al. | 606/86 A |
| 6,203,543 | B1 | * | 3/2001 | Glossop | 606/60 |
| 6,226,548 | B1 | * | 5/2001 | Foley et al. | 600/426 |
| 6,443,955 | B1 | | 9/2002 | Ahrend et al. | |
| 6,482,208 | B1 | | 11/2002 | Ahrend et al. | |
| 6,503,251 | B1 | | 1/2003 | Shadduck | |
| 6,529,765 | B1 | * | 3/2003 | Franck et al. | 600/427 |
| 6,551,325 | B2 | * | 4/2003 | Neubauer et al. | 606/88 |
| 6,607,561 | B2 | | 8/2003 | Brannon | |
| 6,679,888 | B2 | * | 1/2004 | Green et al. | 606/86 R |
| 6,856,828 | B2 | * | 2/2005 | Cossette et al. | 600/429 |
| 6,993,374 | B2 | * | 1/2006 | Sasso | 600/426 |
| 7,063,705 | B2 | * | 6/2006 | Young et al. | 606/86 R |
| 7,520,879 | B2 | * | 4/2009 | Justis et al. | 606/86 A |
| 7,547,307 | B2 | * | 6/2009 | Carson et al. | 606/88 |
| 7,862,568 | B2 | * | 1/2011 | Vilsmeier et al. | 606/86 R |

(Continued)

FOREIGN PATENT DOCUMENTS

EP 1 523 950 A1 4/2005

*Primary Examiner* — Kevin T Truong
*Assistant Examiner* — Christopher Beccia
(74) *Attorney, Agent, or Firm* — Renner, Otto, Boisselle & Sklar, LLP

(57) ABSTRACT

A device for fixing a reference element with respect to a field of surgery includes a first fixing portion operable to provide a mechanical resistance against pulling and/or pushing forces, a second fixing portion provided with a surface structure operable to secure the device against an angular force, and a coupling structure. The coupling structure is operative to mechanically couple the second fixing portion to the first fixing portion, wherein said second fixing portion can be pivoted with respect to the first fixing portion.

9 Claims, 2 Drawing Sheets

U.S. PATENT DOCUMENTS

| | | | |
|---|---|---|---|
| 2002/0183759 A1* | 12/2002 | Green et al. | 606/86 |
| 2003/0009169 A1* | 1/2003 | Young et al. | 606/86 |
| 2003/0028196 A1* | 2/2003 | Bonutti | 606/87 |
| 2003/0078565 A1* | 4/2003 | Vilsmeier et al. | 606/1 |
| 2004/0019263 A1* | 1/2004 | Jutras et al. | 600/407 |
| 2004/0172044 A1* | 9/2004 | Grimm et al. | 606/130 |
| 2005/0020920 A1* | 1/2005 | Ritland | 600/459 |
| 2008/0045861 A1* | 2/2008 | Miller et al. | 600/567 |

* cited by examiner

DEVICE FOR FIXING A REFERENCE ELEMENT

RELATED APPLICATION DATA

This application claims priority of U.S. Provisional Application Nos. 60/754,510 and 60/754,553, both filed on Dec. 28, 2005, which are incorporated herein by reference in their entirety.

FIELD OF THE INVENTION

The present invention relates to a device and method for fixing a reference element in relation to a surgical field, such as, for example, a human or animal bone.

BACKGROUND OF THE INVENTION

Minimally invasive operations require a high degree of accuracy in order to guarantee short hospital stays and quick recovery times. Often in such operations, however, the operations are performed deep within the patient's body and, therefore, the surgeon does not have direct visual access to the surgical workspace. To assist the surgeon in this regard, reference arrays or the like, in conjunction with navigation systems, for example, may be used to provide information and guidance to the surgeon with respect to the surgical workspace. Such reference arrays may be fixed to an area of interest such that they may be visible to particular sighting methods, such as X-rays, ultrasonic methods, optical methods (including light in the infrared spectrum), or the like, so that information regarding the distances, shapes and operations in the surgical workspace may be obtained.

As will be appreciated, once the reference elements or reference arrays are calibrated, they cannot be shifted or displaced with respect to their original location. A displacement of the reference array or of one or more reference elements may divert the surgeon from the actual situation in the surgical workspace and, thus, might cause surgical errors.

In the prior art, there are many different devices that may be used when operating on an injured bone. In this respect, reference is made, for example, to U.S. Pat. No. 6,607,561, U.S. Pat. No. 6,503,251, U.S. Pat. No. 6,482,208, U.S. Pat. No. 6,443,955, U.S. Pat. No. 5,688,285, U.S. Pat. No. 4,927,421 and U.S. Pat. No. 4,759,350, said prior art references all being directed to the use of surgical fixing devices for fixing ligaments, bone parts, bones and so on.

SUMMARY OF THE INVENTION

The above prior art does not discuss ensuring a location of a reference element or reference array such that a minimally invasive surgical operation may be performed by means of image-guided surgical operation techniques.

According to one aspect of the invention, a device for fixing a reference element, reference array, or the like, includes a first fixing portion for providing a mechanical resistance against pulling and/or pushing forces, and a second fixing portion mechanically connected by a coupling structure to the first fixing portion. The second fixing portion may be provided with a surface structure in order to secure the device against an angular force, wherein the second fixing portion can be pivoted with respect to the fixed, first fixing portion.

By means of this device, it is possible to guarantee the attachment of any surgical means to an object such that displacement is not possible. In other words, the attached device can be fixed, in particular to a bone, such that the translational and rotational stability of the location of the device can be guaranteed.

A method for fixing the above device includes providing an access to the surgical workspace and then introducing the device into the surgical workspace. The bone is penetrated with the first fixing portion, and the second fixing portion is pivoted towards a surface of the bone. The surface structure of the second fixing portion then can be urged against and/or into the surface of the bone.

The principles for the present invention also can be applied to fixing devices for other surgical instruments, wherein said instruments can be secured at a particular location in a surgical field and prevented from being displaced during a surgical operation. In particular, the device and the method are useful for image guided surgical methods and for computer aided surgical methods. Vector Vision/Trauma 2.5, which are known products of the assignee of the present invention, are directed to such surgical methods.

One reference element or a number of reference elements, in particular a reference array, can be fixed to the device, in particular to order to allow an image-guided surgical operation method to be used.

The first fixing portion can be a bolt, a screw or the like (e.g., a surgical Schanz screw or the like). The diameter of the screw preferably is about 5 mm so as to provide the device with sufficient fixing strength as the first fixing portion is penetrated into the bone (and in particular drilled into the bone). Preferably a bone thickness of at least 4 and preferably 5 mm remains around the insertion point of the screw so as to minimize the likelihood of bone spalling. The screw preferably is drilled monocortically into the bone structure of interest.

The second fixing portion can have a first segment with a pivoting structure which is close to the coupling structure, such that the first and the second fixing portions may be pivotally coupled to each other. This structure allows the second fixing portion to be rotated or pivoted towards the surface of a bone, such that it is possible to provide another fixing location without serious injury to the bone itself. By means of the first and second fixing portion, it is possible to clamp the bone between them. The first fixing portion, because of the fixing function of the second fixing portion, cannot then be rotated.

The direction of an axis of the first fixing portion, e.g., the screw or Schanz screw, is preferably tangential to the bone surface so as to ensure the subsequent attachment of the second fixing portion. If the second fixing portion has the preferred shape of a fork, the fork shape can be inserted through the soft tissue entry portal into the body of the patient such that the two or more prongs are respectively located to the left and right of the first fixing portion, e.g., a Schanz screw and the Schanz screw rests in a U-shaped upper part of the fork.

The second fixing portion may be provided with a second lever segment supporting the surface structure that is to be urged against the surface of the bone. An offset segment may be provided between the second lever segment and a first lever segment. This offset segment allows the fixation area for the first fixing portion and the surface structure at one end of the second fixing portion, e.g., of the second lever segment, to be offset. The device described herein can be used for several different bones and bone shapes, and the offset segment can help to adapt the device to different bone shapes.

The second fixing portion can include a shoulder segment for pivotally supporting the second fixing portion during a fixing operation action. If the first fixing portion is advanced into the bone to a certain degree and comes into engagement with a stopping structure in the second fixing portion close to the coupling structure, the second fixing portion can be rotated about the shoulder segment such that the surface structure of the second fixing portion can be urged against the surface of the bone merely by drilling or screwing the first fixing portion, in particular a screw, into the bone.

A connecting element can be engaged with the first fixing portion, wherein the connecting element can include a protrusion for extending through a recess or hole in the first lever segment. The protrusion may be engaged with a fixing element for urging the surface structure towards the bone surface and for holding the surface structure in this position. The connecting element preferably can be a bushing and the protrusion can be a threaded shaft or pin. The fixing element can be realized as a thumb screw so that a considerable force can be applied by a surgeon without having to use a particular tool.

The pivoting and urging steps for the second fixing portion can be performed by adjusting the fixing element, e.g., a thumb screw, towards the first lever segment.

To summarize, the present invention provides an attachment device and an attachment method that enable attachment of a device to a bone. Preferably, a surgical Schanz screw having a diameter of at least 5 mm and a fork-shaped second fixing portion are used. The first fixing portion or Schanz screw (having a diameter of about least 4-5 mm or more) may be drilled monocortically into the bone structure. Preferably, a bone thickness of at least 5 mm remains around the first fixing portion, e.g., the Schanz screw. The direction of the screw axis should be tangential to the bone surface so as to ensure the subsequent attachment. The fork-shaped structure can be inserted through a soft tissue entry portal into the patient's body such that two prongs of the fork-shaped structure can be located to the left and right of the screw, respectively. As will be appreciated, a different number of prongs can also be used (e.g., instead of two prongs, three or four prongs can be used that have differently shaped offset segments that can be extended or contracted in length, etc.). Such additional features could be added to adapt the device to different bone shapes in the human or animal body. Preferably, the screw rests in a U-shaped upper part of the fork or second fixing portion, e.g., in the first lever segment, which may be located beyond the shoulder segment and thus beyond the center of rotation of the second fixing portion.

A cylindrical bushing can be used achieve a sufficient stability in attaching the device, wherein the bushing can be placed over the Schanz screw. The threaded pin can be connected to the bushing and extend radially outward from the cylinder axis of the bushing, the cylinder axis also being the axis of the screw. The thumb screw or wing nut can be screwed towards the bushing in order to urge the fork towards the Schanz screw, such that the lower or second lever segment with the surface structure is urged against the surface of a bone. This then attaches the device, which provides a considerable resistance against pulling and pushing forces, such that the device can be positioned in a translationally and rotationally stable manner.

BRIEF DESCRIPTION OF THE DRAWINGS

The forgoing and other features of the invention are hereinafter discussed with reference to the drawings.

DETAILED DESCRIPTION

Figure 1A:
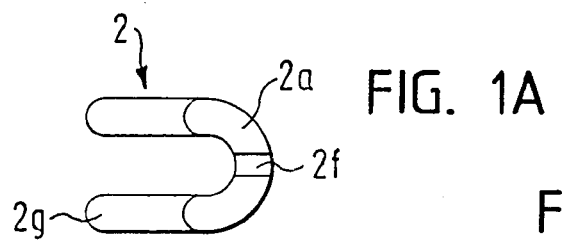
FIGS. 1A-1C show a top view (1A), a first side view (1B) and a second side view (1C) of a second portion of an exemplary fixing device in accordance with the invention.

In the detailed description that follows, corresponding components have been given the same reference numerals, regardless of whether they are shown in different embodiments of the present invention.

Figure 1B:
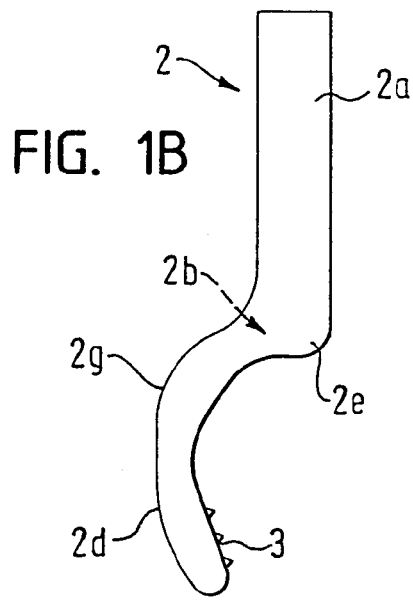
Figure 1C:
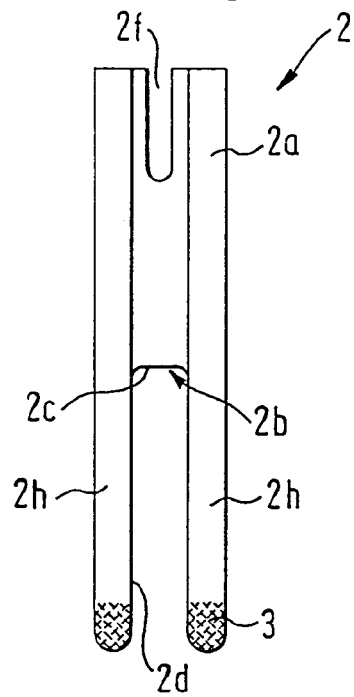

FIGS. 1A-1C illustrate a second fixing portion 2 of an exemplary fixing device in accordance with the present invention. The second fixing portion 2 has a fork shape, and includes a shaft 2a having a U-shaped cross section. The fork-shaped portion is provided with two prong extensions 2h which comprise the second lever segment 2d of the second fixing portion 2. An upper part of the portion 2 includes the first lever segment 2a. The second lever segment 2d and the first lever segment 2a are connected to each other by an offset segment 2g. On the lower part of the first lever segment 2a, a shoulder segment 2e is provided which, for example, can be shaped like a mandrel or a bolt. A surface structure 3 can be provided at the end of the second lever segment 2d, e.g., at the end of one or both of the prong extensions 2h. This surface structure 3 can be shaped as spikes, ridges or the like, in order allow of the surface structure 3 to be securely fixed when it is attached to the surface of a bone.

The U-shaped structure of the upper or first lever segment 2a helps to secure a first fixing portion within the clearance of the U-shaped cross section of the second fixing portion 2. A center of rotation 2b is provided close to the shoulder segment 2e, between the offset segment 2g and the first lever segment 2a. The first lever segment 2a can also have a recess or hole 2f for attaching additional fixing elements.

Figure 2:
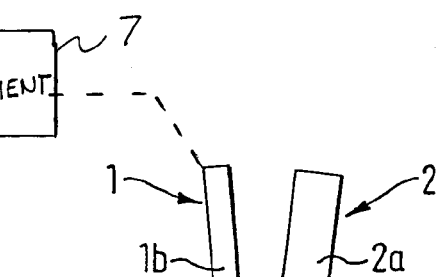
FIG. 2 shows a first portion of an exemplary fixing device in accordance with the invention, wherein the first portion is fixed to a bone and coupled to the second portion.
Figure 2:
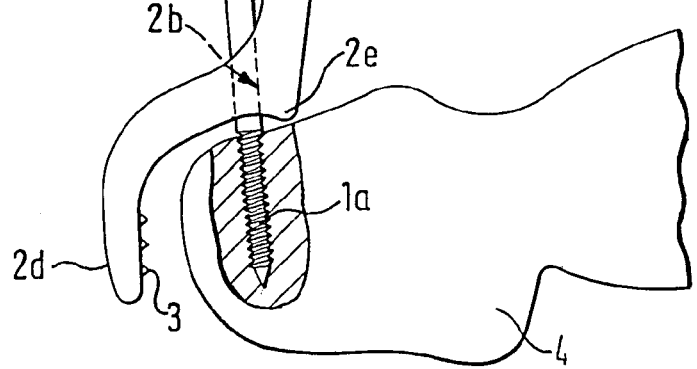

With further reference to FIG. 2, a first fixing portion 1 has penetrated into the bone structure, which in the present case is a proximal femur, for example. The first fixing portion 1 comprises a shaft portion 1b and a threaded portion 1a which can be drilled or screwed into the bone 4. By advancing the screw, in particular a Schanz screw, into the bone, the Schanz screw can be stopped in its axial sliding movement within the U-shaped portion of the second fork-shaped fixing portion 2 and can urge the shoulder segment 2e against the surface of the bone. Consequently, if the first fixing portion 1 is advanced further into the bone, the second lever segment 2d is rotated about the center of rotation 2b and the shoulder segment 2e, such that the surface structure 3 is moved towards and urged against the surface of the bone so as to stably attach the device to the bone structure 4.

A device 7, such as a medical instrument or reference star, for example, can be attached to the first and/or second fixing portions 1 and 2. The device may be attached to the first and/or second fixing portions via any suitable means.

Figure 3A:
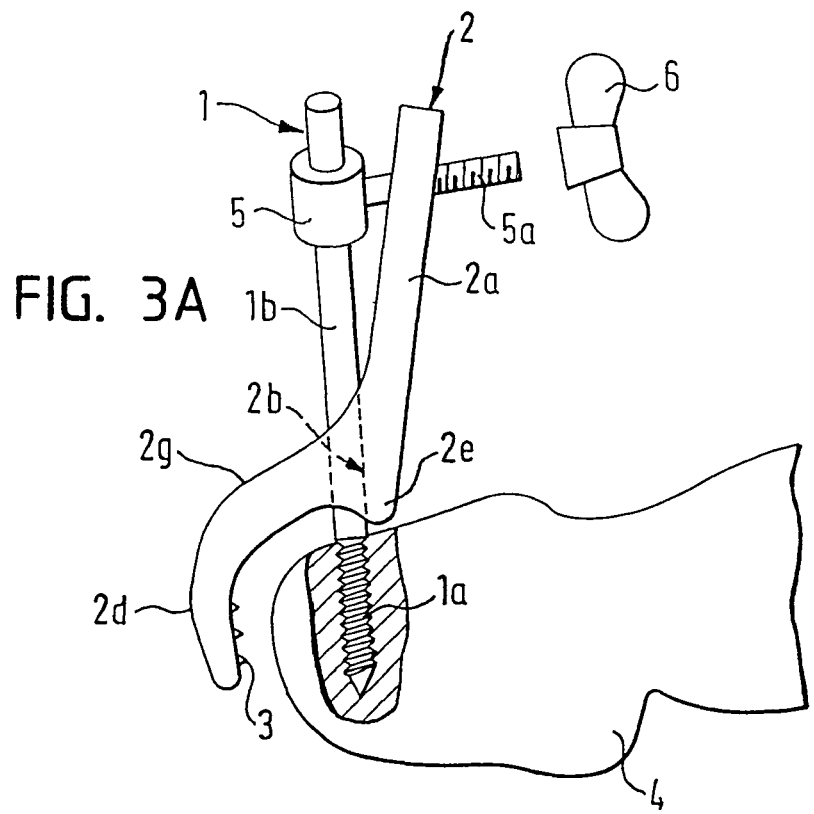
FIGS. 3A-3B show a perspective view of the exemplary fixing device in accordance with the invention, wherein the fixing device includes a securing mechanism
Figure 3B:
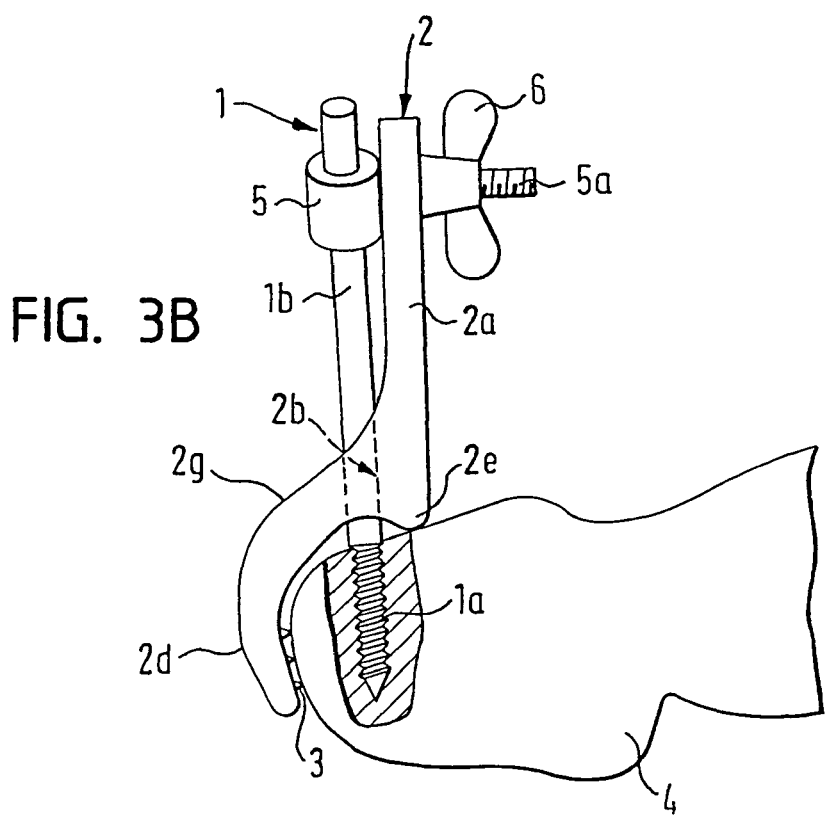

Moving now to FIGS. 3A-3B, a connecting element 5 can be provided, which in this example is a bushing element 5. The cylindrical bushing element 5 is placed over the first fixing portion 1, in particular a Schanz screw, and the threaded extension 5a is extended through a recess or hole (2f in FIGS. 1A and 1C). A wing nut or thumb screw 6 acts as a fixing element for rotating the first lever segment 2 towards the first fixing portion 1. By means of this pivoting movement of the first lever segment 2a, the second lever segment 2d, which can include two or more prong extensions 2h, is rotated toward the surface of the bone structure 4. The surface structure 3 can be urged against the surface of the bone structure 4, as shown in FIG. 3B.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A device for fixing a reference element with respect to a field of surgery including a bone, comprising:
    a first fixing portion operable to provide a mechanical resistance against pulling and/or pushing forces, wherein said first fixing portion is a bolt or a screw configured to be introduced into the bone;
    a second fixing portion provided with a surface structure operable to secure the device to the bone against an angular force; and
    a coupling structure operative to mechanically couple the second fixing portion to the first fixing portion, wherein said second fixing portion is pivotable with respect to the first fixing portion, wherein said second fixing portion comprises a first lever segment with a pivoting structure having a pivot surface such that the first and second portions are pivotally coupled to each other, and wherein the pivot surface is movable into abutting engagement with the first fixing portion and pivots against the first fixing portion.

2. The device according to claim 1, wherein the screw is a surgical Schanz screw.

3. The device according to claim 1, wherein the first lever segment is located at about the coupling structure.

4. The device according to claim 1, wherein a connecting element is engaged with the first fixing portion, said connecting element having a protrusion for extending through a recess or hole in the first lever segment, said protrusion being engaged with a fixing element for pivotally urging the surface structure towards a surface of the bone.

5. The device according to claim 1, wherein said second fixing portion includes a second lever segment operable to support the surface structure.

6. The device according to claim 1, wherein said second fixing portion includes a shoulder segment operable to pivotally support the second fixing portion.

7. The device according to claim 1, wherein the second fixing portion is formed to have at least two prong extensions extending on respective sides of the first fixing portion towards a lower end of the first fixing portion.

8. The device according to claim 1, wherein the surface structure includes a plurality of spikes or ridges.

9. The device according to claim 7, wherein the at least two prong extensions are laterally spaced apart in a first direction and the pivot surface is formed between the prong extensions.

* * * * *